United States Patent [19]

Bayer et al.

[11] 4,076,741
[45] Feb. 28, 1978

[54] HERBICIDAL 4-TRIFLUOROMETHYL-4-NITRODIPHE-NYL ETHERS

[75] Inventors: Horst O. Bayer, Levittown; Colin Swithenbank, Perkasie; Roy Y. Yih, Doylestown, all of Pa.

[73] Assignee: Rohm and Haas Company, Philadelphia, Pa.

[21] Appl. No.: 331,947

[22] Filed: Feb. 12, 1973

Related U.S. Application Data

[63] Continuation-in-part of Ser. No. 234,656, Mar. 14, 1972, Pat. No. 3,888,932.

[51] Int. Cl.$^2$ .................. C07C 121/75; C07C 43/20
[52] U.S. Cl. ........................ 260/465 F; 260/612 R; 71/105; 71/124
[58] Field of Search ............ 260/612 R, 465 F, 465 G

[56] References Cited

U.S. PATENT DOCUMENTS

| | | | |
|---|---|---|---|
| 3,420,892 | 1/1969 | Martin et al. | 260/612 R |
| 3,798,276 | 3/1974 | Bayer et al. | 260/612 R |
| 3,888,932 | 6/1975 | Bayer et al. | 260/612 R |

FOREIGN PATENT DOCUMENTS

| | | | |
|---|---|---|---|
| 870,561 | 3/1953 | Germany | 260/612 |

*Primary Examiner*—Bernard Helfin

[57] ABSTRACT

Compounds of the formula

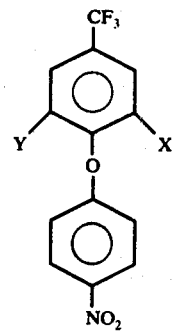

wherein
 X is a hydrogen atom, a halogen atom, a trihalomethyl group, an alkyl group, or a cyano group, and
 Y is a hydrogen atom, a halogen atom, or a trihalomethyl group,
and compositions containing these compounds exhibit herbicidal activity.

7 Claims, No Drawings

HERBICIDAL 4-TRIFLUOROMETHYL-4-NITRODIPHENYL ETHERS

CROSS-REFERENCE TO RELATED APPLICATION

This application is a continuation-in-part of our copending application Ser. No. 234,656, filed on Mar. 14, 1972, now U.S. Pat. No. 3,888,932, granted June 19, 1975.

This invention relates to novel compounds which show activity as herbicides, to novel herbicidal compositions which contain these compounds, and to new methods of controlling weeds with these herbicidal compositions.

Certain diphenyl ethers have been shown to be effective weed control agents. However, the herbicidal effectiveness of a given diphenyl ether cannot be predicted from an examination of the substituent groups attached to the phenyl rings in the ether, and often quite closely related compounds will have quite different weed control abilities. Various diphenyl ethers may have overlapping or complementary areas of activity or selectivity, and can thus be useful in combination to control a variety of weeds upon application of a single composition. Furthermore, the diphenyl ethers heretofore disclosed as herbicides are not completely effective. An ideal herbicide should give selective weed control, over the full growing season, with a single administration at low rates of application. It should be able to control all common weeds by killing them as the seed, the germinating seed, the seedling, and the growing plant. At the same time, the herbicide should not be phytotoxic to the crops to which it is applied and should decompose or otherwise is dissipated so as not to poison the soil permanently. The known diphenyl ether herbicides fall short of these ideals, and it would thus be desirable to have new herbicides which show even more selective control of undesirable plants among desirable crop plants or which complement the known diphenyl ethers in activity.

In accordance with the present invention, there is provided a new class of novel diphenyl ethers having the formula

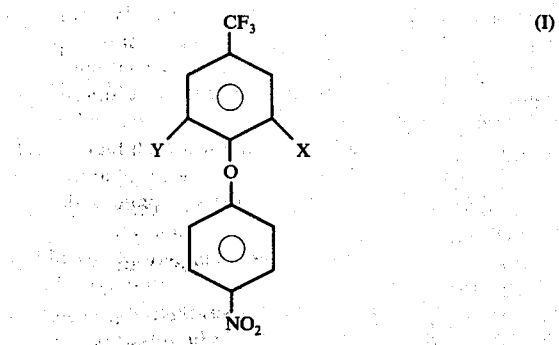

wherein
X is a hydrogen atom, a halogen atom, preferably a fluorine atom or a chlorine atom, a trihalomethyl group, preferably a trifluoromethyl group, a $(C_1-C_4)$alkyl group, preferably a methyl group, or a cyano group, and Y is a hydrogen atom, a halogen atom, preferably a fluorine atom or a chlorine atom, or a trihalomethyl group, preferably a trifluoromethyl group.

The alkyl portion of the alkyl-containing X substituents can have either a straight- or branched-chain or a cyclic spatial configuration. These novel compounds have been found to show unexpected activity as weed control agents. In a preferred embodiment of the invention, X is a halogen atom or a cyano group, and Y is an hydrogen atom or a halogen atom.

Examples of the compounds of the invention embraced by Formula I include:

α,α,α-trifluoro-p-tolyl-4-nitrophenyl ether,
2,α,α,α-tetrafluoro-p-tolyl-4-nitrophenyl ether,
2-bromo-α,α,α-trifluoro-p-tolyl-4-nitrophenyl ether,
2-chloro-α,α,α-trifluoro-p-tolyl-4-nitrophenyl ether,
α,α,α-trifluoro-2-iodo-p-tolyl-4-nitrophenyl ether,
2,6-dichloro-α,α,α-trifluoro-p-tolyl-4-nitrophenyl ether,
2-chloro-α,α,α-tetrafluoro-p-tolyl-4-nitrophenyl ether,
2-cyano-α,α,α-trifluoro-p-tolyl-4-nitrophenyl ether,
2-cyano-6,α,α,α-tetrafluoro-p-tolyl-4-nitrophenyl ether,
2-cyano-6-chloro-α,α,α-trifluoro-p-tolyl-4-nitrophenyl ether,
α,α,α,α',α'-hexafluoro-2,4-xylyl-4-nitrophenyl ether,
6-chloro-α,α,α,α',α',α'-hexafluoro-2,4-xylyl-4-nitrophenyl ether,
$α^4,α^4,α^4$-trifluoro-2,4-xylyl-4-nitrophenyl ether,
2-butyl-α,α,α-trifluoro-p-tolyl-4-nitrophenyl ether,
2-chloro-6-ethyl-α,α,α-trifluoro-p-tolyl-4-nitrophenyl ether,
and the like.

The novel diphenyl ethers of the invention are useful both as preemergence and as postemergence herbicides. Preemergence herbicides are ordinarily used to treat the soil in which the desired crop is to be planted by application either before seeding, during seeding, or, as in most applications, after seeding and before the crop emerges. Postemergence herbicides are those which are applied after the plants have emerged and during their growth period.

Among the crops on which the diphenyl ethers of the invention can be advantageously employed are, for example, cotton, soybeans, peanuts, beans, peas, carrots, corn, and other cereal crops.

The diphenyl ethers of the invention are useful for controlling weeds in rice crops. When used in transplanted rice crops, the ethers can be applied either preemergence or postemergence to the weeds — that is, they can be applied to the transplanted rice plants and their growth medium either before the weed plants have emerged or while they are in their early stages of growth. The ethers can be applied to the growth medium either before or after the rice has been transplanted to that medium.

The diphenyl ethers of the invention can be applied in any amount which will give the required control of weeds. A preferred rate of application of the herbicides of the invention is from about 0.1 to about 12 pounds of the diphenyl ether per acre.

Under some conditions, the diphenyl ethers of the invention may be advantageously incorporated into the soil or other growth medium prior to planting a crop. This incorporation can be carried out by any convenient means, including by simple mixing with the soil, by applying the diphenyl ether to the surface of the soil and then disking or dragging into the soil to the desired depth, or by employing a liquid carrier to accomplish the necessary penetration and impregnation.

A diphenyl ether of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers 1969 Annual."

The diphenyl ether compounds of this invention can be dissolved in any appropriate solvent. Examples of solvents which are useful in the practice of this invention include alcohols, ketones, aromatic hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the diphenyl ether can be dissolved in organic solvents, such as benzene, toluene, xylene, methylated naphthalene, corn oil, pine oil o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or other grain-hulls, or similar material. A solution of one or more of the diphenyl ethers in a volatile organic solvent can be sprayed or mixed with the granular solid and the solvent then removed by evaporation. The granular material can have any suitable size, with a preferable size range of 16 to 60 mesh. The diphenyl ether will usually comprise about 2 to 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formulations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low-gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

Carboxylic Acids and Derivatives 2,3,6-trichlorobenzoic acid and its salts
2,3,5,6-tetrachlorobenzoic acid and its salts
2-methoxy-3,5,6-trichlorobenzoic acid and its salts 2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salt and esters
2,3,6-trichlorophenylacetic acid and its salts
3,6-endoxohexahydrophthalic acid
dimethyl-2,3,5,6-tetrachloroterephthalate
trichloroacetic acid and its salts
2,2-dichloropropionic acid and its salts
2,3-dichloroisobutyric acid and its salts

Carbamic Acid Derivatives ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate

Phenols dinitro-o-(sec-butyl)phenol and its salts
pentachlorophenol and its salts

Substituted Ureas 3-(3,4-dichlorophenyl)-1,1-dimethylurea
3-phenyl-1,1-dimethylurea
3-(3,4-dichlorphenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea dichloral urea

Substituted Triazines 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropylamino-s-triazine

Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether
2,4-dichloro-3'-methoxy-4'-nitrodiphenyl ether

Anilides

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-α,α-dimethylvaleramide
N-isopropyl-N-phenylchloroacetamide
N-n-butoxymethyl-N-(2,6-diethylphenyl)chloroacetamide
N-n-methoxymethyl-N-(2,6-diethylphenyl)chloroacetamide

Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

Nitriles 2,6-dichlorobenzonitrile
diphenylacetonitrile
3,5-dibromo-4-hydroxybenzonitrile
3,5-diiodo-4-hydroxybenzonitrile

Other Organic Herbicides 2-chloro-N,N-diallylacetamide
N-(1,1-dimethyl-2-propynyl)-3,5-dichlorobenzamide
maleic hydrazide
3-amino-1,2,4-triazole
monosodium methanearsonate
disodium methanearsonate
N,N-dimethyl-α,α-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
O-(2,4-dichlorphenyl)-O-methyl-isopropylphosphoramidothioate
4-amino-3,5,6-trichloropicolinic acid
2,3-dichloro-1,4-naphthoquinone
di(methoxythiocarbonyl)disulfide
3-isopropyl-1H-2,1,3-benzothiadiazine-(4)3H-one-2,2-dioxide
6,7-dihydrodipyridol[1,2-a:2',1'-c]pyrazidinium salts
1,1'-dimethyl-4,4'-bipyridinium salts
3,4,5,6-tetrahydro-3,5-dimethyl-2-thio-2H-1,3,5-thiadiazine.

When mixtures of herbicides are employed, the relative proportions which are used will depend upon the crop to be treated and the degree of selectivity in weed control which is desired.

The diphenyl ethers of the invention or their precursors can be prepared by reacting a suitably substituted phenol, or the potassium or sodium salt of the phenol, with a suitably substituted halobenzene, such as a chloro- or fluorobenzene, in the presence of an alkaline agent.

The following examples will further illustrate this invention but are not intended to limit it in any way. In Table I, typical diphenyl ethers of the invention are listed with their melting points and elemental analyses. Specific, illustrative preparations of the compounds of Examples 1 to 3 and 6 to 8 are described after Table I.

TABLE I
Diphenyl Ethers - Physical Data

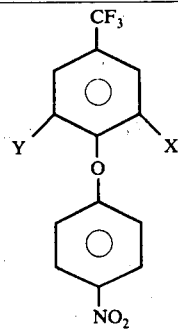

|  |  |  |  |  | Analysis |  |  |  |  |
|---|---|---|---|---|---|---|---|---|---|
| Example No. | X | Y | m.p.(b.p.)° C |  | %C | %H | %N | %Cl | %F |
| 1 | CN | H | 93–98 | found | 54.83 | 2.33 | 9.29 |  | 15.84 |
|  |  |  |  | reqs. | 54.56 | 2.29 | 9.09 |  | 18.49 |
| 2 | Cl | H | 67–70 | found | 49.31 | 2.15 | 4.44 | 11.15 | 17.80 |
|  |  |  | $C_{13}H_7ClF_3NO_3$ | reqs. | 49.19 | 2.22 | 4.41 | 11.21 | 17.94 |
| 3 | F | H | (95–98/0.35 mm) | found | 51.77 | 2.50 | 4.77 |  |  |
|  |  |  | $C_{13}H_7F_4NO_3$ | reqs. | 51.16 | 2.31 | 4.59 | 15.73 | 26.21 |
| 4 | Br | H | 86–87 | found | 43.44 | 1.78 | 3.63 | 22.13* | 15.85 |
|  |  |  | $C_{13}H_7BrF_3NO_3$ | reqs. | 43.10 | 1.95 | 3.87 | 22.07* | 15.74 |
| 5 | H | H | 47–48 | found | 55.42 | 3.00 | 4.73 |  | 19.85 |
|  |  |  | $C_{13}H_8F_3NO_3$ | reqs. | 55.12 | 2.85 | 4.95 |  | 20.13 |
| 6 | Cl | Cl | 83–86 | found | 44.24 | 1.42 | 4.04 | 20.15 | 15.98 |
|  |  |  | $C_{13}H_6Cl_2F_3NO_3$ | reqs. | 44.33 | 1.72 | 3.98 | 20.13 | 16.19 |
| 7 | $CH_3$ | H | 58–63.5 | found | 56.15 | 3.50 | 5.29 |  | 18.93 |
|  |  |  | $C_{14}H_{10}F_3NO_3$ | reqs. | 56.57 | 3.39 | 4.71 |  | 19.18 |
| 8 | $CF_3$ | H | 72–73 | found | 48.33 | 2.09 | 3.81 |  | 30.48 |
|  |  |  | $C_{14}H_7F_6NO_3$ | reqs. | 47.87 | 2.01 | 3.09 |  | 32.46 |

*%Br

EXAMPLE 1

Preparation of 2-cyano-α,α,α-trifluoro-p-tolyl-4-nitro phenyl ether

A solution of potassium hydroxide (3.2 g. 0.05 mole of 89.3% purity) and p-nitrophenol (7.0 g. 0.05 mole) in methanol (25 ml.) is stripped under reduced pressure. The residue is dissolved in sulfolane, 4-chloro-3-cyano α,α,α-trifluorotoluene (10.3 g. 0.05 mole) added, and the resulting solution heated at 150° C for 5 hours. After cooling, the solution is diluted with benzene (350 ml.) washed with water (6 × 250 ml.), dried, and the solvent removed. The residue (12.5 g.) is recrystallized from isopropanol to give 2-cyano-α,α,α-trifluoro-p-tolyl-4-nitrophenyl ether (7.6 g., 49%) m.p. 93°–98° C.

EXAMPLE 2

Preparation of 2-chloro-α,α,α-trifluoro-p-tolyl-4-nitro phenyl ether

Ia. 2-Chloro-α,α,α-trifluoro-p-cresol

Chlorine gas is passed through a flow meter into a solution of α,α,α-trifluoro-p-cresol (4.05 g. 0.025 mole) in ethylene dichloride (200 ml.) at 0° C. until the theoretical volume has been absorbed. The solvent is stripped off and the residue distilled to give 2-chloro-α,α,α-trifluoro-p- cresol (3.5 g. 71%) b.p. 80°–82° C. at 33 mm.

Ib. 2-Chloro-α,α,α-trifluoro-p-tolyl-4-nitrophenyl ether

Potassium hydroxide (1.08 g. 0.0166 mole, 86% pure) is dissolved in methanol (10 ml.) and a solution of 2-chloro-α,α,α-trifluoro-p-cresol (3.27 g. 0.0166 mole) in methanol added. The solvent is removed under pressure and sulfolane (100 ml.) added followed by p-fluoronitrobenzene (2.34 g., 0.0166 mole) and the mixture heated at 130–150° C for 7 hours. After cooling, the solution is poured into water (200 ml.) and extracted with benzene. The extract is dried, filtered through activated silica gel (10 g.) and the solvent removed. The residue is taken up in isopropanol/hexane (1:3) cooled to −20° C, decanted from an oily precipitate, and the solvents stripped off. The residue (2.9 g.) is distilled to give 2-chloro-α,α,α-trifluoro p-tolyl-4-nitrophenyl ether (1.6 g. 31%) b.p. 23°–85° C/ 0.3 mm which when induced to crystallize has a melting range of 62°–68° C. An impurity isolated from a preparation following this procedure has been identified as 4-carbomethoxy-2-chlorophenyl-4-nitrophenyl ether.

IIa. 2Chloro-α,α,α-trifluoro-p-tolyl phenyl ether

Potassium phenoxide, prepared by stripping a solution of phenol (4.7 g. 0.05 moles) and potassium hydroxide (3.3 g. 0.05 moles 86.2% purity) in methanol (20 ml.) is dissolved in sulfolane (75 g), and 3,4-dichloro α,α,α-trifluorotoluene (10.8 g., 0.05 mole) added. The mixture is heated at 170° C overnight then cooled, diluted with benzene (250 ml.), and washed with water (3 × 600 ml.). The organic phase is dried, filtered through activated silica gel (20 g.) and the solvent removed. The residue (12.4 g.) is distilled to give 2-chloro-α,α,α-trifluoro-p tolyl phenyl ether (9.9 g. 72%) b.p. 85–90° C/ 0.25 mm. contaminated with about 5% of 6-chloro-α,αλ ,α-trifluoro m- tolyl phenylether.

Found: C, 57.13; H, 3.09; Cl, 13.17; F, 20.86 Calculated for $C_{13}H_8ClF_3O$; C, 57.27; H, 2.95; Cl, 13.00; F, 20.91.

b. 2-Chloro-α,α,α-trifluoro-p-tolyl-4-nitrophenyl ether

A mixture of fuming nitric acid (10 g. 0.16 mole) and concentrated sulfuric acid (10 g.) is added with vigorous stirring to 2-chloro-α,α,α-trifluoro-p-tolyl phenylether (27.3 g. 0.01 mole) initially at 75° C, maintaining a rate of addition such that the temperature does not rise above 85° C. After stirring at 80° C for one half hour, further mixed acid (5 g. + 5 g.) is added and the mixture stirred for fifteen minutes, cooled, diluted with water, an extracted with benzene (2 × 200 ml.). The extract is washed with water and bicarbonate solution, dried, and the solvent removed. The residue (29.1 g.) is recrystallized from isopropanol to give 2-chloro-α,α,α-trifluoro-p-tolyl-4-nitrophenyl ether (12.7 g. 40%) m.p. 67°–70° C. Analytical and spectroscopic data confirm the identity of the products from Routes I and II.

EXAMPLE 3

Preparation of 2, α,α,α-Tetrafluoro-p-tolyl-4-nitrophenyl ether a. 2-Amino-α,α,α-trifluoro-p-tolylphenyl ether 2-Nitro-α,α,α-trifluoro-p-tolylphenyl ether (57.0 g., 0.209 mole) is dissolved in ethanol (200 ml.) and shaken in an atmosphere of hydrogen in a Parr apparatus in the presence of platinum oxide (100 mg.) until uptake is complete. The catalyst is removed by filtration and the solvent stripped off to give 2-amino-α,α,α-trifluoro-p-tolyl phenylether (50.3 g. 99%) which is used without further purification.

Found: C, 61.76; H, 3.65; F, 22.35; N, 5.52. Calculated for $C_{13}H_{10}F_3NO$; C, 61.66; H, 3.98; F, 22.51; N, 5.53.

b. 2,α,α,α-tetrafluoro-p-tolylphenyl ether

2-Amino-α,α,α-trifluoro-p-tolylphenyl ether (25.3 g., 0.1 mole) is added to concentrated hydrochloric acid (100 ml.) and the mixture cooled to −15° C. A solution of sodium nitrite (7.5 g. 0.1 + mole) in water (5 ml.) is added dropwise with stirring, and after a total of 2 hours at −15° C, the diazonium chloride solution is filtered and treated with a solution of sodium fluoroborate (25 g. 0.2 + mole) in water (30 ml.) and the dense fluborate salt filtered off and washed with ethanol and ether, then air dried, yield 23.0 g., decomposition point ~ 190° C. The salt is then added portionwise to a flask maintained in an oil bath at 200° C, and when decomposition is complete, the residue is taken up in benzene (150 ml.), washed with water (4 × 100 ml.), dried, and the solvent removed. The residue (10.3 g.) was extracted with isopropanol/hexane to give a residue which on distillation gives 2,α,α,α-tetrafluoro-p-tolylphenyl ether (3.4 g. 14%), b.p. 90° C/0.25 mm.

c. 2,α,α,α-tetrafluoro-p-tolyl-4-nitrophenyl ether

The above material is nitrated by the procedure described in Example 2 above for 2-chloro-α,α,α-tetrafluoro-p-tolyl-4-nitrophenyl ether.

EXAMPLE 6

Preparation of 2,6-Dichloro-α,α,α-trifluoro-p-tolyl-4-nitrophenyl ether a. 3,4-Dichloro-α,α,α-trifluoro-5-nitro toluene and 3,4-dichloro-α,α,α-trifluoro-6-nitro toluene A mixture of 3,4-dichloro-α,α,α-trifluorotoluene (430 g., 2.0 moles), concentrated sulphuric acid (1200 ml.) and concentrated nitric acid (1200 ml., excess) was stirred at 90°–100° C for one half hours. The mixture was then cooled and the acid phase discarded. The organic phase was washed with water, dilute sodium bicarbonate solution, potassium carbonate solution, dried, and distilled to give an approximately equal mixture (456 g., 89%) of 3,4-dichloro-α,α,α-trifluoro-5-nitrotoluene and 3,4-dichloro-α,α,α-trifluoro-6-nitrotoluene, b.p. 86° C/3 mm.

b. 2-Chloro-α,α,α-trifluoro-6-nitro-p-tolylphenyl ether

A solution of potassium hydroxide (43.2 g. of 86% pure, 0.665 moles) in water (20 ml.) was added slowly to a mixture of phenol (62.5 g., 0.665 mole) and the product from (a) above 450 g. total, equivalent to 0.665 mole of 3,4-dichloro-α,α,α-trifluoro-5-nitro toluene) in sulfolane (300 ml.) at 30°–68° C. with stirring. After stirring at 42°–68° C for a total of one hour the mixture was diluted with hexane (400 ml.) and water (600 ml.). The resulting layers were separated and the aqueous phase extracted once with hexane. The combined organic phases were washed with water and dilute caustic soda solution, dried and the solvent removed. The residue (471.3 g.) was distilled through a vacuum jacketed Vigreux column. No. 1 (272.2 g.) bp < 100° C/0.2 mm. consisted essentially of unreacted 3,4-dichloro-α,α,α-trifluoro-6-nitrotoluene. No. 2 (196.2 g.) b.p. 109°–119° C/0.2 mm. was essentially pure desired diphenylether. A small residue (3.5 g.) was discarded. No. 2 crystallized and was recrystallized from 2-propanol (600 ml.) at 0° C. to give 2-chloro-α,α,α-trifluoro-6-nitro-p-tolylphenyl ether (144 g. 68%) m.p. 57°–61° C.

c. 2-Amino-6-chloro-α,α,α-trifluoro-p-tolylphenyl ether

A solution of 2-chloro-α,α,α-trifluoro-6-nitro-p-tolylphenyl ether (150 g., 0.472 mole) in ethanol (1200 ml.) was shaken in an atmosphere of hydrogen in a Parr apparatus in the presence of $PtO_2$ (600 mg.) until uptake ceased. The catalyst was filtered off, the solvent removed, and the residue taken up in pentane (600 ml.) and filtered through activated silica gel (~ 15 g.) and the solvent removed. The residue was recrystallized from pentane at −20° C. to give 2-amino-6-chloro-α,αλ ,α-trifluoro-p-tolylphenyl ether (94.1 g., 70%) m.p. 47–53° C.

d. 2,6-Dichloro-α,α,α-trifluoro-p-tolylphenyl ether

2-Amino-6-chloro-α,α,α-trifluoro-p-tolylphenyl ether (5.8 g., 0.02 moles) was ground with concentrated hydrochloric acid (70 ml.) to give a suspension of the amine hydrochloride. A solution of sodium nitrite (1.5 g., 0.022 moles) in water (3 ml.) was added dropwise to the stirred suspension at −15° C then the mixture was stirred for fifty minutes at +3 < <10° C then filtered through a sintered glass filter. The filtrate was slowly added to a suspension of cuprous chloride (3.0 g.) in concentrated hydrochloric acid (20 ml.) at −3− −10° C, then the temperature was slowly raised, finally to 90° C for twenty minutes. The mixture was then cooled and neutralized with solid sodium bicarbonate and extracted with ether. The extract was washed with water and sodium carbonate solution, dried and stripped. The residue was distilled, to give the diphenylether (3.5 g.) as an oil which crystallized. The solid was taken up in pentane (10 ml.) and filtered through activated silica gel (∼ 5 g.) and the solvent removed. The residue (3.3 g.) was recrystallized from 2-propanol to give 2,6-dichloro-α,α,α-trifluoro-p-tolylophenyl ether (2.75 g. 45%) m.p. 48-50° C.

e. 2,6-Dichloro-α,α,α-trifluoro-p-tolyl-4-nitrophenyl ether 2,6-Dichloro-α,α,α-trifluoro-p-tolylphenyl ether (1.7 g., 0.0055 mole) was added to a cold (0° C) mixture of concentrated sulphuric acid (1.7 g.) and concentrated nitric acid (1.2 g.). The mixture was warmed to 30°–35° C and stirred at this temperature for 30 minutes, then diluted with water and extracted with benzene/pentane, and the extract washed with sodium bicarbonate solution and water, then dried and stripped. The residue was combined with the result of a similar experiment on 500 mg. of starting material and recrystallized from 2-propanol to give 2,6-dichloro-α,α,α-trifluoro-p-tolyl-4-nitrophenyl ether (1.9 g., 75%) m.p. 83–86° C.

EXAMPLE 7

Preparation of $\alpha^4,\alpha^4,\alpha^4$-trifluoro-2,4-xylyl-4-nitrophenyl ether a. 2-Bromo-α,α,α-trifluoro-p-tolylphenyl ether A solution of 3-bromo-4-chloro-α,α,α-trifluoro-toluene (143 g., 0.55 mol), potassium phenoxide (72.6 g. 0.55 mol), in sulfolane (200 ml.) is heated and stirred 3 hours at 165°–170° C. The solution is cooled. Benzene (250 ml.) and hexane (250 ml.) are added, and the solution washed with dilute sulfuric acid (500 ml.), the solvent removed, and the oil distilled to give 2-bromo-α,α,α-trifluoro-p-tolylphenyl ether (124 g., 71%) b.p. 100°–105° C./0.45mm.

b. $\alpha^4,\alpha^4, \alpha^4$-trifluoro-2,4-xylylphenyl ether n-Butyl lithium, 15%/hexane solution (50 ml., 0.083 mol) is added to a stirred solution of 2-bromo-α,α,α-trifluoro-p-tolylphenyl ether (25.36 g., 0.08 mol) and hexane (300 ml.) under nitrogen and stirred 10 minutes at 25° C. dimethylsulfate (25 g. 0.2 mol) is added in one lot and the mixture is refluxed gently for 10 minutes, poured onto ice and the aqueous phase discarded. The hexane solution is washed with water, dried, the solvent removed and the oil distilled to give $\alpha^4,\alpha^4, \alpha^4$-trifluoro-2,4-xylylphenyl ether, b.p. 86°–88° C./0.3 mm.

c. $\alpha^4,\alpha^4,\alpha^4$-trifluoro-2,4-xylyl-4-nitrophenyl ether

A cooled mixture of concentrated sulfuric acid (14 ml., 0.25 mol) and concentrated nitric acid (14 ml, 0.22 mol) is added to a stirring solution of 2-methyl-α,α,α-trifluoro-p-tolylphenyl ether (17.8 g., 0.07 mol) and 1,2-dichloroethane (60 ml.) at 6°–14° C. in 74 minutes and stirred for 70 minutes at 10°–15° C. The oil layer is separated, washed with water, 10% sodium carbonate solution, and twice with water; the solvent is removed, and the product crystallized from hexane-isopropanol to give $\alpha^4,\alpha^4, \alpha^4$-trifluoro-2,4-xylyl-4-nitrophenyl ether (6.3 g., 30%) m.p. 58°–63.5° C.

EXAMPLE 8

Preparation of α,α,α,α′,α′,α′-hexafluoro-2,4-xylyl-4-nitrophenyl ether a. α,α,α,α′,α′,α′-hexafluoro-2,4-xylylphenyl ether A solution of potassium phenoxide (15.0 g. 0.1 m) and 4-chloro-α,α,α,α′,α′,α′-hexafluoro-m-xylene in sulfolane (50 ml.) is heated 60 hours at 140°–160° C. The solution is cooled and benzene (400 ml.) and hexane (250 ml.) are added and the solution washed twice with water (1 liter, 500 ml.), twice with 10% sodium carbonate solution (∼200 ml. each), and water, dried, filtered through activated silica gel (18 25 g.), the solvents removed, and the residue distilled to give α,α,α,α′,α′,α′-hexafluoro-2,4-xylylphenyl ether (22.4 g., 73%) b.p. 81°–85° C./∼ 1 mm.

b. α,α,α,α′,α′,α′-hexafluoro-2,4-xylyl-4-nitrophenyl ether

α,α,α,α′,α′,α′-Hexafluoro-2,4-xylyl phenyl ether ether (16.1 g. 0.0525 mol), concentrated sulfuric acid (12 ml. 0.22 mol), concentrated nitric acid (12 ml. 0.19 mol) and ethylene dichloride (65ml) are stirred 30 minutes at room temperature and allowed to separate. The ethylene dichloride layer is washed with water, 10% sodium carbonate solution, and water and the solvent removed. The residual oil is dissolved in hexane, filtered through activated silica gel (18 25 g.) and the solvent removed to give α,α,α,α′,α′,α′-hexafluoro-2,4-xylyl-4-nitrophenyl ether (11.4 g. 62%) m.p. 72°–73° C.

EXAMPLES 9–14

Following the procedures of Examples 1 to 3, other diphenyl ethers of Formula I are prepared. Among the compounds which are prepared by these procedures are: 6-chloro-α,α,α,α′,α′,α′-hexafluoro-2,4-xylyl-4-nitrophenyl ether, 2-chloro-6,α,α,α-tetrafluoro-p-tolyl-4-nitrophenyl ether, α,α,α-trifluoro-2-iodo-p-tolyl-4-nitrophenyl ether, 2-cyano-6-chloro-α,α,α-trifluoro-p-tolyl-4-nitrophenyl ether, 2-bromo-$\alpha^4,\alpha^4,\alpha^4$-4,6-xylyl-4-nitrophenyl ether, and 2-chloro-α,α,α,α′,α′,α′-4,6-xylyl-4-nitrophenyl ether. These diphenyl ethers have herbicidal properties.

It should be noted that the diphenyl ethers of the invention can also be named correctly using different systems of nomenclature. For example, the diphenyl ether of Example 1can also be named as 2-cyano-4-trifluoromethyl4′-nitrodiphenyl ether. However, within the specification and claims of this invention the Chemical Abstracts system of nomenclature, as exemplified in Examples 1–13, has been followed.

The following examples show the herbicidal properties of the diphenyl ethers of the invention.

EXAMPLE 15

This example shows the herbicidal activity of diphenyl ethers of the invention towards a number of common weeds. Using the procedure described below, diphenyl ethers were evaluated for control of the following weeds: At 10 pounds per acre:

| Monocots | Dicots |
|---|---|
| barnyardgrass (Echinochloa crus.) | bindweed (Convolvulus arvensis) |
| crabgrass (Digitaria spp.) | curly dock (Rumex crispus) |
| nutsedge (Cyperus esculentus) | velvetleaf (Abutilon theophrasti) |
| wild oats (Avena fatua) | wild mustard (Brassica haber) |

At 2 and 4 pounds per acre:
Monocots
barnyardgrass (Echinochloa crusgalli)
**Bermudagrass (Cynodon dactylon)
crabgrass (Digitaria spp.)
*downy brome (Bromus tectorum)
foxtail (Setaria faberii)
Johnsongrass (Sorghum halepense)
nutsedge (Cyperus esculentus)
quackgrass (Agropyron repens)
*ryegrass (Lolium perenne)
*wild oats (Avena fatua)
*yellow millet (Panicum miliaceum)
Dicots
bindweed (Convolvulus arvensis)
cocklebur (Xanthium pensylvanicum)
**coffeeweed (Sesbania macrocarpa)
*curly dock (Rumex crispus)
*lambsquarters (Chenopodium album)
morningglory (Iopmoea purpurea)
*pigweed (Amaranthus retroflexus)
**ragweed (Ambrosia artemisiifolia)
*smartweed (Polygonum pensylvanicum)
**tomato (Lycopersicon esculentum)
velvetleaf (Abutilon theophrasti)
*wild carrot (Daucus carota)
*wild mustard (Brassica haber)

*Examples 1 to 5 only
**Examples 6 to 8 only

The following test procedure is employed. Seeds of selected crops and weeds are planted in soil in flats. For preemergence tests, the flats are treated with the test compound immediately after the planting. For postemergence tests, the seeds are allowed to germinate, and after two weeks the flats are treated with the test compound. The compound to be evaluated is dissolved in acetone, diluted with water, and sprayed over the flats using a carrier volume equivalent to 50 gallons per acre at the rate of application (pounds per acre, lb/A.) specified in the tables. About two weeks after the application of the test compound, the state of growth of the plants is observed and the phytotoxic effect of the compound is evaluated. Table II gives the average percent control achieved by the test compounds in terms of the percent of the plants which are killed by the compounds.

nomic crops. Following the test procedure of Example 15, diphenyl ethers of the invention are evaluated for significant tolerance (as shown by 50% or less kill of the test crop at levels of application which give more than 50% kill of many or all of the weeds of Example 15) towards some or all of the following common agronomic crops (not all compounds tested against all crops): alfalfa, snapbeans, corn, cotton, cucumbers, peanuts, rape, rice, soybeans, tomatoes, and wheat.

Tolerance to snapbeans in preemergence applications is shown by the compounds of Examples 1, 2 and 6. Tolerance to corn in preemergence applications is shown by the compounds of Examples 1 and 2 and in postemergence applications by the compounds of Examples 1, 2, and 6. Tolerance to cotton in preemergence applications is shown by the compounds of Examples 1, 2, and 6 and in postemergence or layby applications by

TABLE II

| Compound of Example No. | lb./A. | HERBICIDAL ACTIVITY (% control) Preemergence | | | Postemergence | | |
|---|---|---|---|---|---|---|---|
| | | 10 | 4 | 2 | 10 | 4 | 2 |
| 1 | M* | 96 | 82 | 71 | 99 | 75 | 74 |
|   | D* | 97 | 52 | 51 | 100 | 74 | 81 |
| 2 | M | 77 | 96 | 96 | 100 | 99 | 92 |
|   | D | 97 | 100 | 88 | 100 | 92 | 85 |
| 3 | M | 94 |   | 96 | 100 |   | 87 |
|   | D | 95 |   | 71 | 100 |   | 77 |
| 4 | M | 87 | 99 |   | 100 | 94 |   |
|   | D | 100 | 83 |   | 100 | 94 |   |
| 5 | M | 0 | 73 |   | 77 | 19 |   |
|   | D | 0 | 39 |   | 90 | 49 |   |
| 6 | M |   | 100 |   |   | 86 |   |
|   | D |   | 100 |   |   | 99 |   |
| 7 | M |   | 86 | 75 |   | 34 | 46 |
|   | D |   | 85 | 73 |   | 73 | 92 |
| 8 | M |   | 81 | 72 |   | 24 | 35 |
|   | D |   | 82 | 78 |   | 70 | 73 |

*M = Monocots;
*D = Dicots

EXAMPLE 16

This example shows the selective herbicidal activity of diphenyl ethers of the invention in a number of agrothe compound of Example 1. Tolerance to peanuts in preemergence applications is shown by the compounds of Examples 1 and 2. Tolerance to soybeans in preemergence applications is shown by the compounds of Examples 1 and 2 and in postemergence or layby applications by the compound of Example 2. Tolerance to rice in preemergence applications is shown by the compounds of Examples 1 and 2 and in postemergence applications or in applications on transplanted rice by the compounds of Examples 1, 2, and 8. Tolerance to wheat in preemergence and postemergence applications is shown by the compounds of Examples 1, 2, and 6.

It is to be understood that changes and variations may be made without departing from the spirit and scope of the invention as defined by the appended claims.

We claim:

1. A compound of the formula

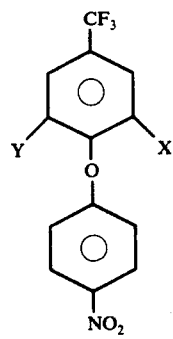

wherein
X is a hydrogen atom, a trifluoromethyl group, a $(C_1-C_4)$ alkyl group, or a cyano group, and
Y is a hydrogen atom, a halogen atom, or a trifluoromethyl group, provided that when X is a hydrogen atom, Y is other than a halogen atom.

2. A compound according to claim 1 wherein Y is a hydrogen atom.

3. A compound according to claim 2 wherein X is a cyano group.

4. A compound according to claim 2 wherein X is a methyl group.

5. A compound according to claim 2 wherein X is a hydrogen atom.

6. A compound according to claim 1 wherein Y is a halogen atom.

7. The compound of the formula

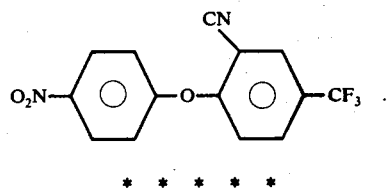

* * * * *